US00PP07936P

United States Patent [19]

Hanes

[11] Patent Number: Plant 7,936

[45] Date of Patent: Aug. 11, 1992

[54] GERANIUM NAMED AMERICANA LIGHT SALMON

[75] Inventor: Mitchell Hanes, Morgan Hill, Calif.

[73] Assignee: Goldsmith Seeds, Inc., Gilroy, Calif.

[21] Appl. No.: 656,707

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new and distinctive Geranium cultivar particularly distinguished by its light salmon colored double flowers, its green foliage and vigorous growth and superior cutting productivity.

1 Drawing Sheet

BACKGROUND OF THE NEW PLANT

The present invention comprises a new and distinct cultivar of Geranium, botanically known as *Pelargonium hortorum* Bailey. The new cultivar is propagated from a seedling resulting from the cross of a seed parent "Regina" and the pollen parent "Pink Camellia."

This new cultivar is a product of a planned breeding program intended to create new Geranium cultivars with light salmon colored flowers, semi-double flower form, green foliage, vigorous growth and superior cutting productivity.

This new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of this new geranium cultivar. The data which defines these characteristics were collected from asexual reproductions carried out by Goldsmith Seeds, Inc. in Gilroy, Calif. The plant history was taken on 9 week old plants, blossomed under natural light in a greenhouse and color readings were taken in the greenhouse (in Gilroy, Calif.) on Sep. 26, 1990 at 2 P.M. under ambient light. Color references are primarily to The RHS Colour Chart of The Royal Horticultural Society of London, England.

THE PLANT

Classification:

*Botanical.*—*Pelargonium hortorum* Bailey.

*Commercial.*—Zonal geranium.

Form: Upright bush.

Height: Seven and one half to nine and one half cm., as a 5½ inch pot plant, excluding blooms.

Growth: Vigorous.

Strength: Fast-rooting, free flowering plant, with good shipping ability as rooted or unrooted cuttings.

Foliage: Abundant quantity.

Leaves:

*Size.*—Diameter about 6 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 3 to 4 cm. long.

*Color.*—Upper side: Green with light red zonation on the younger leaves fading to a dark green zone on the older leaves. Underside: Lighter green color. Ribs and veins not prominently different from upper surface.

Petioles: About 3 to 4 cm. in length.

THE BUD

Size:

*Diameter.*—About 8 mm.

*Length.*—About 1.5 cm. to 1.7 cm. at time of bud opening.

Shape: Pointed ovoid.

Color: Of petals when sepals first divide, RHS 33-B.

Sepals: Five in number, flat behind petals. Pointed linear lanceolate, RHS 144-B in an open flower.

THE FLOWER

Blooming habit: Continuous throughout the year.

Size: Approximately 4.5 cm. diameter, 1.0 cm. deep, irregularly radially symmetrical.

Form: Cup-shaped when bloom first opens, later flattening to shallow cup shape with maturity.

Petals: Five imbricate outer petals, 2.5–2.8 cm. wide and approximately 2.5 cm. long. Four to seven inner smaller petaloids of varying shape. Both the outer petals and inner petaloids are salmon RHS 43-D and fade lighter to the outer margin, RHS 55-D. Veins slightly darker than interveinal regions. Color changing little with age. Underside of petals are much lighter. Petals and petaloids soft and satiny.

Pedicel: Approximately 2.5–3.0 cm. in length.

Persistence: Nonshattering flower.

INFLORESCENSE

Type: An umbel composed of approximately 35 flowers, erect or laterally ascending.

Peduncle: Approximately 10–11.5 cm. in length.

REPRODUCTIVE ORGANS

Stamens:

*Anthers.*—Seven–ten positioned below the mature stigma, dull red prior to anthesis.

*Filaments.*—White near base and mid length, graduating to dull red near anther.

*Pollen.*—Orange in color.

Pistil:

*Number.*—One.

*Length.*—Approximately 6 mm.

*Stigma.*—Five or six linear lobes of near equal length, curling back toward ovary, purplish-red.

Style:

*Length.*—About 3 mm., color: purplish-red.

Ovaries: At anthesis, densely pubescent with white hairs, oblong. Green drying to a light brown at maturity.

Fruit: Partially fertile.

I claim:

1. A new and distinct cultivar of Geranium substantially as herein shown and described, characterized by its green foliage, salmon/light salmon bi-color colored, semi-double flowers on large umbels, the plant being fast-rooting and vigorous.

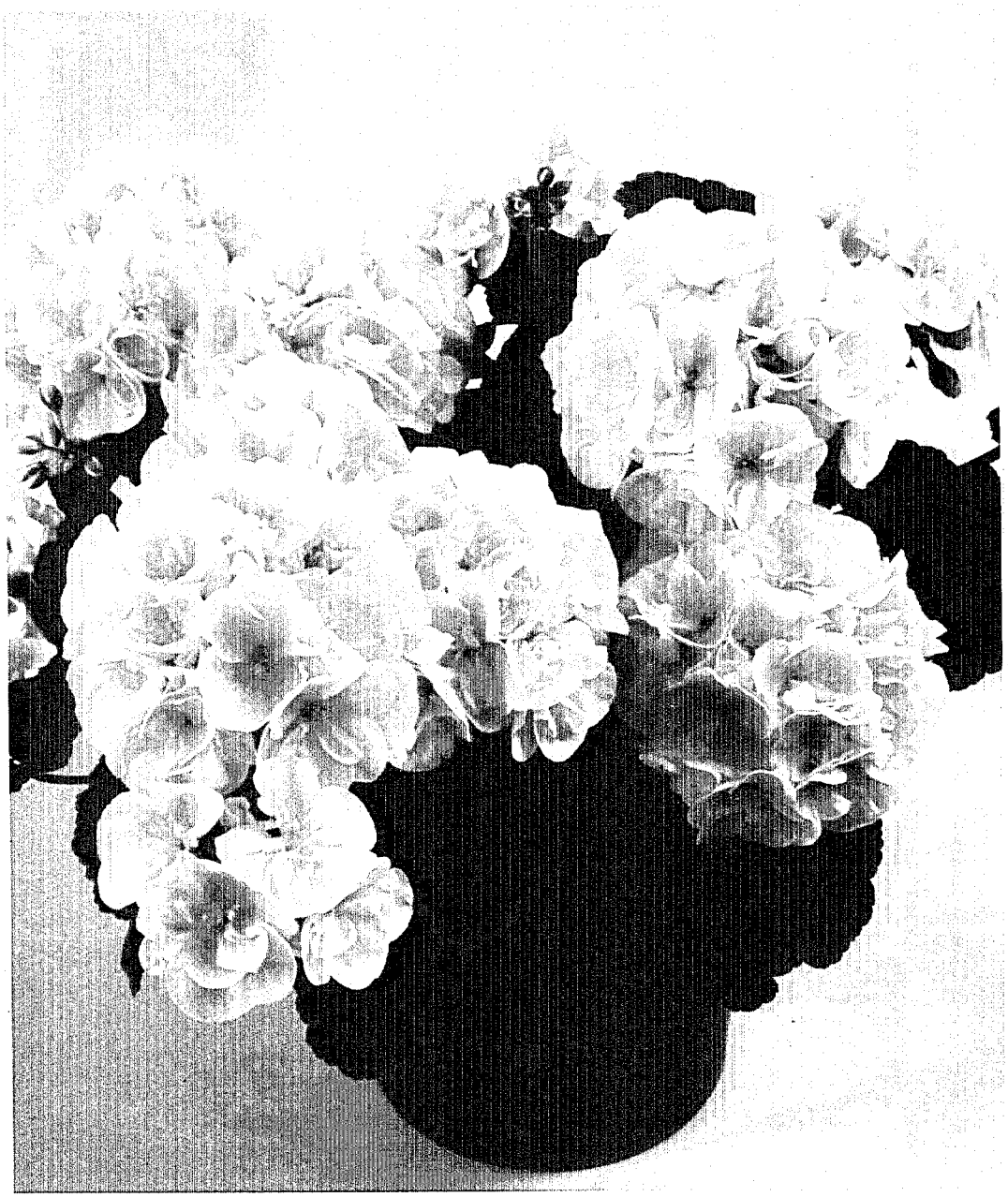

* * * * *